(12) United States Patent
Ueki

(10) Patent No.: US 7,760,365 B2
(45) Date of Patent: Jul. 20, 2010

(54) ASPHERIC LENS SURFACE-DECENTER MEASURING METHOD AND APPARATUS

(75) Inventor: Nobuaki Ueki, Saitama (JP)

(73) Assignee: FUJINON Corporation, Saitama-shi (JP)

(*) Notice: Subject to any disclaimer, the term of this patent is extended or adjusted under 35 U.S.C. 154(b) by 300 days.

(21) Appl. No.: 12/047,580

(22) Filed: Mar. 13, 2008

(65) Prior Publication Data

US 2008/0304080 A1   Dec. 11, 2008

(30) Foreign Application Priority Data

Mar. 29, 2007   (JP)   ............... P2007-089308

(51) Int. Cl.
G01B 11/02 (2006.01)
(52) U.S. Cl. ................................. 356/515
(58) Field of Classification Search ............ 356/511, 356/512, 515, 497
See application file for complete search history.

(56) References Cited

U.S. PATENT DOCUMENTS

| | | | | |
|---|---|---|---|---|
| 4,848,907 | A * | 7/1989 | Yokokura et al. | 356/458 |
| 4,974,950 | A * | 12/1990 | Yamazaki et al. | 359/557 |
| 5,039,223 | A * | 8/1991 | Gemma et al. | 356/458 |
| 5,737,079 | A * | 4/1998 | Burge et al. | 356/513 |
| 5,877,850 | A * | 3/1999 | Ogata | 356/3.04 |
| 5,999,251 | A * | 12/1999 | Teramoto et al. | 356/127 |
| 6,072,570 | A * | 6/2000 | Chipman et al. | 356/124 |
| 6,717,651 | B2 * | 4/2004 | Kato et al. | 355/55 |
| 7,098,433 | B2 * | 8/2006 | Suzuki et al. | 250/201.9 |
| 7,151,596 | B2 * | 12/2006 | Takahashi et al. | 356/138 |
| 7,535,557 | B2 * | 5/2009 | Wu et al. | 356/127 |
| 7,580,122 | B2 * | 8/2009 | Huang et al. | 356/124 |
| 2002/0080366 | A1 | 6/2002 | Nakayama | |
| 2005/0179911 | A1 * | 8/2005 | Boomgarden et al. | 356/512 |

FOREIGN PATENT DOCUMENTS

| | | |
|---|---|---|
| JP | 2951366 B2 | 7/1999 |
| JP | 11-237311 | 8/1999 |
| JP | 2000-97618 | 4/2000 |
| JP | 3127003 B2 | 11/2000 |
| JP | 2002-206915 | 7/2002 |

OTHER PUBLICATIONS

Kim et al., "Use of null optics for monitoring the optical alignment of a beam director," Jul. 10, 2005, Applied Optics, vol. 44, No. 20, pp. 4239-4243.*
D.G. Burns; Null Test for Hyperbolic Convex Mirrors, Applied Optics; vol. 22, No. 1; Jan. 1983.
Korean Office Action; appl. No. 10-2008-0023886.

* cited by examiner

Primary Examiner—Gregory J Toatley, Jr.
Assistant Examiner—Scott M Richey
(74) Attorney, Agent, or Firm—Birch, Stewart, Kolasch & Birch, LLP

(57) ABSTRACT

A relationship between surface decenter of a lens 1 under test and surface-decenter comatic aberration and a relationship between surface tilt of the lens 1 under test and surface-tilt comatic aberration are calculated by computer simulation. The surface tilt of the lens 1 under test is calculated by measuring a transmissive wavefront of a projecting portion 3, and comatic aberration of the lens 1 under test is calculated by measuring a transmissive wavefront of a lens portion 2. The surface-decenter comatic aberration that occurs due to the surface decenter is calculated by subtracting the surface-tilt comatic aberration from the calculated comatic aberration. The surface decenter of the lens 1 under test is calculated based on the calculated surface-decenter comatic aberration.

16 Claims, 3 Drawing Sheets

ASPHERIC LENS SURFACE-DECENTER MEASURING METHOD AND APPARATUS

CROSS-REFERENCE TO RELATED APPLICATIONS

This application is based upon and claims the benefit of priority from the Japanese Patent Application No. 2007-89308 filed on Mar. 29, 2007; the entire contents of which are incorporated herein by reference.

BACKGROUND OF THE INVENTION

1. Technical Field

The invention relates to an aspheric-lens surface-decenter measuring method and apparatus for measuring surface decenter of an aspheric lens for use in various optical devices such as a digital camera and an optical sensor.

2. Description of the Related Art

Recently, most aspheric lenses are formed by molding. However, due to a relative positional misalignment between molds, a surface decenter (a relative positional misalignment between respective axes of two lens surfaces of an aspheric lens) or a surface tilt (a relative inclination misalignment between respective axes of two lens surfaces of an aspheric lens) may occur in the molded aspheric lenses. It is difficult to completely eliminate such a surface decenter or a surface tilt because of structural mechanism of the molds. However, since the surface decenter and the surface tilt are factors that increase aberrations of the molded aspheric lens, it is preferable to correct the molds so as to decrease the aberrations. For this reason, it is important to measure how much the surface decenter and the surface tilt there occur.

Various decentration measuring tools for measuring surface decenter (decentration) of an aspheric lens have been practically used. Moreover, a method described in Japanese Patent No. 3127003 is known as a method for measuring surface decenter and surface tilt of an aspheric lens. This method measures surface decenter and surface tilt of an aspheric lens having a flange-like projecting portion provided to be perpendicular to an optical axis of the lens, using an autocollimator.

Also, aberrations of an aspheric lens can be obtained by measuring a transmissive wavefront using an interferometer. For example, such a method is known that wavefront aberration obtained by measuring transmissive wavefront is expanded using a power series such as the Zernike polynomials to calculate the Seidel's five aberrations (see Japanese Patent No. 2951366).

Recently, demand for an aspheric lens having a high numeric aperture (NA) is growing. In such a high-NA aspheric lens, surface decenter of several micrometers ($\mu m$) and surface tilt of several tens of seconds are acknowledges as a problem, which was not taken seriously in the past.

Meanwhile, there is also a demand for measuring the surface decenter and the surface tilt in a separate manner with high precision. Depending on a type of an optical system, the optical system may be highly sensitive to the surface decenter of the aspheric lens used but less sensitive to the surface tilt thereof. Therefore, if it is possible to measure the surface decenter and the surface tilt separately, it becomes possible to determine as to whether the aspheric lens can be used in the respective optical systems. Moreover, when the aspheric lens is actually used, it is also possible to take measures to correct the surface decenter and the surface tilt.

However, the presently available decentration measuring tools cannot measure the surface decenter and the surface tilt separately and have relatively high measurement error on the order of about 2 micrometers. In addition, the method described in Japanese Patent No. 3127003 has difficulties in measuring the surface decenter at a highly precise level conforming to the recent demands.

SUMMARY OF THE INVENTION

The invention has been made in view of such circumstances and provides a method and an apparatus for measuring surface decenter of an aspheric lens, which enables to measure surface decenter and surface tilt that occur in a manufactured aspheric lens in a separate manner with high precision.

In order to solve the problems, the invention focuses on the fact that comatic aberration of a lens under test can be separated into aberration that occurs due to surface decenter and aberration that occurs due to surface tilt, and measures the surface decenter of the lens under test with high precision separately from the surface tilt thereof.

According to an aspect of the invention, a method for measuring surface decenter that is relative positional misalignment between axes of two lens surfaces of a lens under test, at least one of the two lens surfaces of the lens under test being an aspheric surface, includes: a comatic aberration measurement step of measuring a transmissive wavefront of the lens under test using an interferometer equipped with a null optical element and obtaining a comatic aberration of the lens under test based on an interference fringe image obtained by the measuring; a surface-decenter comatic aberration calculation step of calculating surface-decenter comatic aberration that occurs due to the surface decenter, by subtracting surface-tilt comatic aberration that is obtained in advance and occurs due to surface tilt from the comatic aberration obtained in the comatic aberration measurement step, wherein the surface tilt is a relative inclination misalignment between the axes of the two lens surfaces; and a surface decenter calculation step of calculating the surface decenter based on the surface-decenter comatic aberration calculated in the surface-decenter comatic aberration calculation step. The comatic aberration measurement step, the surface-decenter comatic aberration calculation step and the surface decenter calculation step are performed in this order.

The method for measuring the surface decenter of the aspheric lens may further include, before the surface-decenter comatic aberration calculation step, a surface-tilt comatic aberration simulation step of obtaining a relationship between the surface tilt and the surface-tilt comatic aberration by computer simulation.

In this case, the surface-tilt comatic aberration simulation step may include a surface-tilt null-optical-element position determination step of determining a position of a center axis of a simulation null optical element with respect to a simulation lens under test in the simulation. The surface-tilt null-optical-element position determination step may include performing transmissive wavefront measurement simulations using the simulation null optical element, for the simulation lens under test to which surface tilt is given, with changing a relative position between the center axis of the simulation null optical element and the simulation lens under test plural times during the simulation, obtaining a relationship between the position of the center axis of the simulation null optical element with respect to the simulation lens under test and wavefront aberration of the simulation lens under test from the respective simulation results, and determining the position of the center axis of the simulation null optical element based on the obtained relationship.

Also, the method for measuring the surface decenter of the aspheric lens may further include, before the comatic aberration measurement step, a surface-decenter comatic aberration simulation step of obtaining a relationship between the surface decenter and the surface-decenter comatic aberration by computer simulation.

In this case, the surface-decenter comatic aberration simulation step may include a surface-decenter null-optical-element position determination step of determining a position of a center axis of a simulation null optical element with respect to a simulation lens under test in the simulation. The surface-decenter null-optical-element position determination step may include performing transmissive wavefront measurement simulations using the simulation null optical element, for the simulation lens under test to which surface decenter is given, with changing a relative position between the center axis of the simulation null optical element and the simulation lens under test plural times during the simulation, obtaining a relationship between the position of the center axis of the simulation null optical element with respect to the simulation lens under test and wavefront aberration of the simulation lens under test, from the respective simulation results, and determining the position of the center axis of the simulation null optical element based on the obtained relationship.

Also, the method for measuring the surface decenter of the aspheric lens may further include, before the surface-decenter comatic aberration calculation step: a null-optical-element inclination simulation step of obtaining a relationship between an inclination of the null optical element with respect to an optical axis of the interferometer and a null-optical-element inclination comatic aberration that occurs due to the inclination, by computer simulation; and a null-optical-element inclination measurement step of measuring an actual inclination of the null optical element with respect to the optical axis of the interferometer. The method may further include: calculating comatic aberration that occurs due to the actual inclination of the null optical element measured in the null-optical-element inclination measurement step, from the relationship obtained in the null-optical-element inclination simulation step; and subtracting the calculated comatic aberration from the comatic aberration measured in the comatic aberration measurement step.

Also, the method for measuring the surface decenter of the aspheric lens may further include, before the surface-decenter comatic aberration calculation step: a lens-under-test inclination simulation step of obtaining a relationship between an inclination of the lens under test with respect to an optical axis of the interferometer and a lens-under-test inclination comatic aberration that occurs due to the inclination, by computer simulation; and a lens-under-test inclination measurement step of measuring an actual inclination of the lens under test with respect to the optical axis of the interferometer. The method may further include: calculating comatic aberration that occurs due to the actual inclination of the lens under test measured in the lens-under-test inclination measurement step, from the relationship obtained in the lens-under-test inclination simulation step; and subtracting the calculated comatic aberration from the comatic aberration measured in the comatic aberration measurement step.

Also, the lens under test may have a projecting portion that is provided so as to be perpendicular to the respective axes of the two lens surfaces. The method may further includes, before the surface-decenter comatic aberration calculation step: a surface tilt measurement step of obtaining the surface tilt by measuring a relative inclination misalignment between a front surface of the projecting portion and a rear surface thereof.

According to another aspect of the invention, an aspheric-lens surface-decenter measuring apparatus measures a surface decenter that is relative positional misalignment between axes of two lens surfaces of a lens under test. At least one of the two lens surfaces is an aspheric surface. The apparatus includes an interferometer including a null optical element, and an analyzing device. The analyzing device includes a comatic aberration calculating unit, a surface-decenter comatic aberration calculating unit and a surface decenter calculating unit. The comatic aberration calculating unit obtains a comatic aberration of the lens under test based on an interference fringe image obtained by measuring a transmissive wavefront of the lens under test using the interferometer. The surface-decenter comatic aberration calculating unit calculates a surface-decenter comatic aberration that occurs due to the surface decenter by subtracting surface-tilt comatic aberration that is obtained in advance and occurs due to surface tilt from the comatic aberration calculated by the comatic aberration calculating unit. The surface tilt is relative inclination misalignment between axes of the two lens surfaces. The surface decenter calculating unit calculates the surface decenter based on the surface-decenter comatic aberration calculated by the surface-decenter comatic aberration calculating unit.

The aspheric-lens surface-decenter measuring apparatus may further include an inclination posture changing unit and a 3-axis directional position changing unit. The inclination posture changing unit changes a relative inclination posture between the lens under test and the null optical element. The 3-axis directional position changing unit changes relative positions between the lens under test and the null optical element in three-axis directions. The three axes are perpendicular to each other.

In this case, the aspheric-lens surface-decenter measuring apparatus may further include a null-optical-element center-axis position determining unit that determines a position of a center axis of the null optical element with respect to the lens under test when the 3-axis directional position changing unit performs adjustment. The null-optical-element center-axis position determining unit may obtain a relationship between (i) the position of the center axis of the null optical element with respect to the lens under test and (ii) a wavefront aberration of the lens under test, from results of measurement of respective wavefront aberrations of the lens under test. The measurement is performed while changing a relative position of the center axis of the null optical element with respect to the lens under test plural times. The null-optical-element center-axis position determining unit may determine the position of the center axis of the null optical element based on the obtained relationship.

Also, the aspheric-lens surface-decenter measuring apparatus may further include a null optical element inclination determining unit that determines an inclination of the center axis of the null optical element with respect to the optical axis of the interferometer when the inclination posture changing unit performs adjustment. The null optical element inclination determining unit may separate the comatic aberration of the lens under test and null-optical-element inclination comatic aberration that occurs due to the inclination of the center axis of the null optical element with respect to the optical axis of the interferometer, from results of measurement of respective wavefront aberrations of the lens under test, the measurement being performed while changing a rotation angle of the lens under test with respect to the optical axis of the interferometer plural times. The null optical element inclination determining unit may determine the inclination of the center axis of the null optical element so that the null-optical-element inclination comatic aberration is substantially eliminated.

Also, the aspheric-lens surface-decenter measuring apparatus may further include a lens inclination determining unit that determines an inclination of the lens under test with respect to the optical axis of the interferometer when the inclination posture changing unit performs adjustment. The lens inclination determining unit may separate the comatic aberration of the lens under test and a lens-under-test inclination comatic aberration that occurs due to the inclination of the lens under test with respect to the optical axis of the interferometer, from results of measurement of respective wavefront aberrations of the lens under test. The measurement is performed while changing a rotation angle of the lens under test about the optical axis of the interferometer plural times. The lens inclination determining unit may determine the inclination of the lens under test so that the lens-under-test inclination comatic aberration is substantially eliminated.

Furthermore, the lens under test may have a projecting portion that is provided to be perpendicular to the respective axes of the two lens surfaces. The apparatus may further include a surface-tilt measuring/calculating unit that obtains the surface tilt based on the interference fringe image obtained by measuring a transmissive wavefront of the projecting portion using the interferometer.

Also, the null optical element may be a reflective null optical element or a transmissive null optical element.

In the method and the apparatus for measuring the surface decenter of the aspheric lens according to the invention, the surface-decenter comatic aberration that occurs due to surface decenter is calculated by subtracting the surface-tilt comatic aberration that occurs due to the surface tilt from the comatic aberration of the lens under test calculated by measuring the transmissive wavefront using the interferometer, and the surface decenter of the lens under test is calculated based on the surface-decenter comatic aberration. Accordingly, this method and this apparatus can provide the following advantages.

That is, since the transmissive wavefront of the lens under test is measured using the interferometer equipped with the null optical element, the comatic aberration of the lens under test can be calculated with high precision based on the interference fringe image obtained by the measurement. Also, the relationship between the surface tilt of the lens under test and the surface-tilt comatic aberration and the relationship between the surface decenter of the lens under test and the surface-decenter comatic aberration can be calculated in advance by the computer simulation. Moreover, the results of the computer simulations performed for various cases showed that the surface-tilt comatic aberration and the surface-decenter comatic aberration can be separated from each other and that the surface-decenter comatic aberration can be calculated by subtracting the surface-tilt comatic aberration from the comatic aberration calculated by measuring the transmissive wavefront. Also, the surface tilt of the lens under test can be calculated with high precision based on the results of the measurement of the transmissive wavefront of the projecting portion and the like.

Therefore, according to the invention in which the surface-decenter comatic aberration is calculated by subtracting the surface-tilt comatic aberration from the comatic aberration of the lens under test, calculated by measuring the transmissive wavefront, and the surface decenter of the lens under test is calculated based on the surface-decenter comatic aberration, it is possible to measure the surface decenter and the surface tilt of the lens under test separately with high precision.

BRIEF DESCRIPTION OF THE DRAWINGS

FIGS. 3(A) and 3(B) are schematic diagrams showing the profile of a lens under test, in which FIG. 3(A) is a front view and FIG. 3(B) is a top view.

FIGS. 4(A) to 4(C) are diagrams for explaining surface tilt and surface decenter, in which FIG. 4(A) shows a state in which only the surface tilt occurs, FIG. 4(B) shows a state in which only the surface decenter occurs, and FIG. 4(C) shows a state in which both of the surface tilt and the surface decenter occur.

DETAILED DESCRIPTION OF EMBODIMENTS OF THE INVENTION

Figure 1:
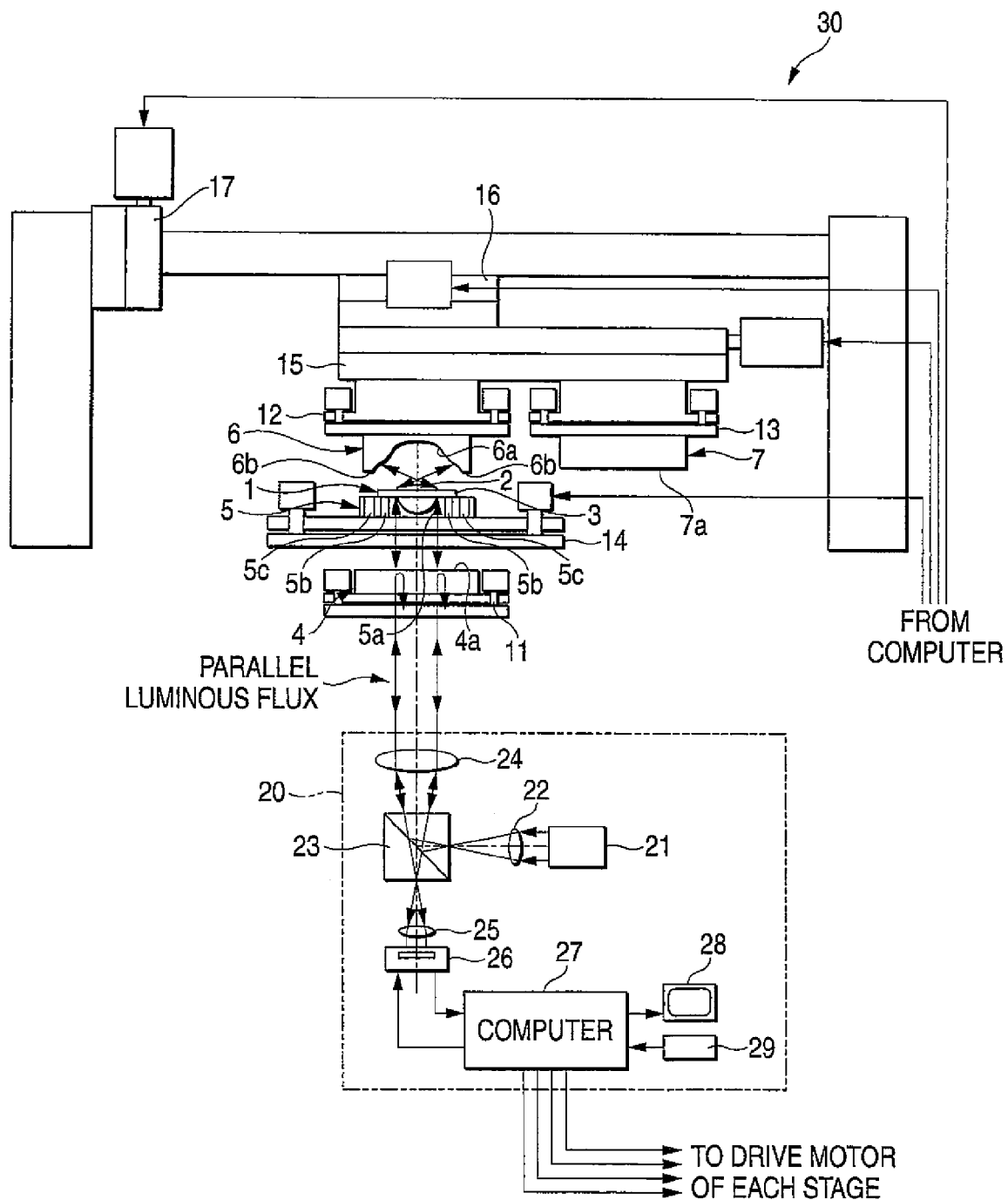
FIG. 1 is a schematic diagram showing the configuration of a surface-decenter measuring apparatus according to an embodiment of the invention.
Figure 2:
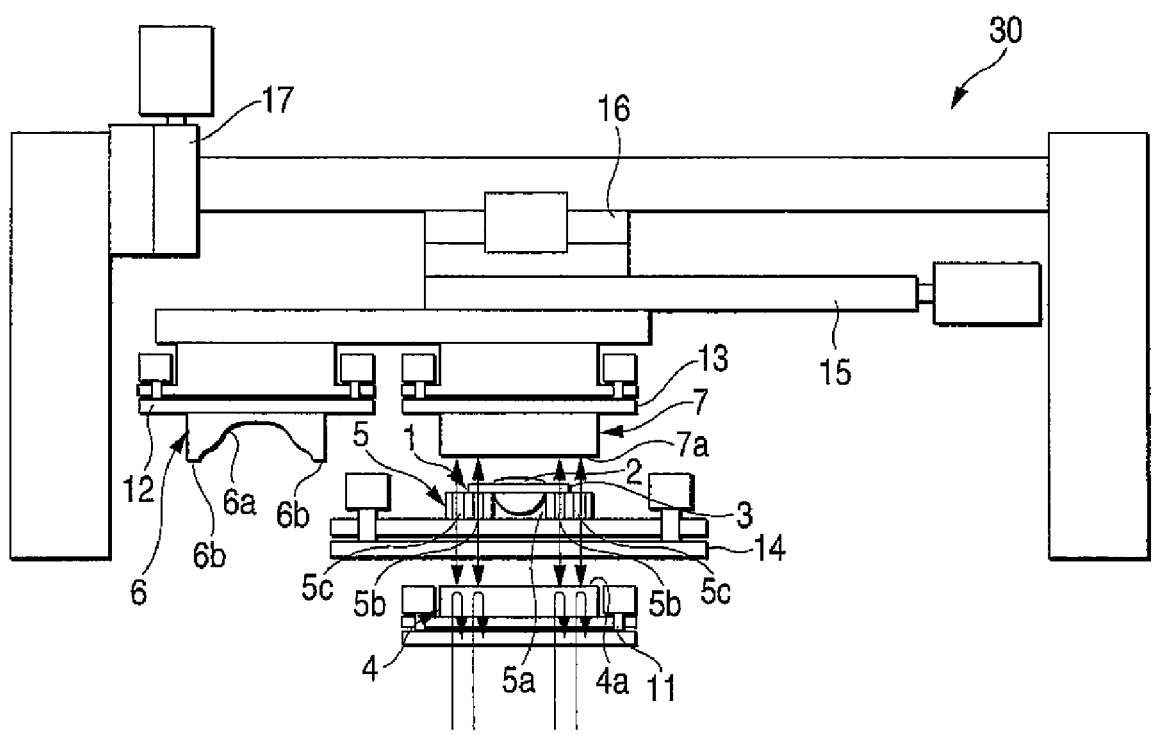
FIG. 2 is a diagram showing a part of the surface-decenter measuring apparatus, in which a reflective reference plate is set.

Hereinafter, embodiments of the invention will be described in detail with reference to the accompanying drawings. FIG. 1 is a schematic diagram showing the configuration of a main part of an aspheric-lens surface-decenter measuring apparatus (hereinafter, simply referred to as "surface-decenter measuring apparatus") according to an embodiment of the invention. FIG. 2 is a diagram showing a part of the surface-decenter measuring apparatus, in which a reflective reference plate is set. FIGS. 3(A) and 3(B) are schematic diagrams showing the profile of a lens under test, in which FIG. 3(A) is a front view and FIG. 3(B) is a top view.

As shown in FIG. 1, the surface-decenter measuring apparatus according to this embodiment includes an interferometer main body 20 and a test object positioning section 30.

The interferometer main body 20 is a Fizeau interferometer device equipped with a light source 21 such as a laser light source having a long coherence length. The interferometer main body 20 includes a beam diameter magnifying lens 22, a beam splitter 23, a collimator lens 24, an image formation lens 25, and an imaging device 26 having a light detecting surface. The interferometer main body 20 is also provided with a computer 27 serving as an analyzing device that performs an image processing operation on images taken by the imaging device 26, various arithmetic operations, and a driving control operation on various adjustment portions, a monitor device 28 for displaying an interference fringe image or the like, and an input device 29 for performing various input operations on the computer 27. A transmissive reference plate 4, a null mirror 6, and a reflective reference plate 7, shown in FIG. 1, are usually included in the interferometer main body 20. However, in this specification, they will be describe as being included in the test object positioning section 30, for the sake of explanation.

The test object positioning section 30 is configured to support and adjust positions of the transmissive reference plate 4, a lens 1 under test, the null mirror 6, and the reflective reference plate 7 used as substitution for the null mirror 6 (see FIG. 2), in this order in the traveling direction (in the upward direction in FIG. 1) of a measurement light flux from the interferometer main body 20.

More specifically, the transmissive reference plate 4 is supported by a manual 2-axis tilt stage 11. Rotation angles (inclinations) of the transmissive reference plate 4 about an X axis (extending in the left-right direction in FIG. 1) and a Y axis (extending perpendicular to the paper of FIG. 1) are adjusted in a preliminary adjustment step. The lens 1 under test is supported by an electric 2-axis tilt stage 14 via a lens mounting jig 5. Rotation angles (inclinations) of the lens 1 under test about the X axis and the Y axis are automatically adjusted at the time of measuring each lens 1 under test. The null mirror 6 and the reflective reference plate 7 are supported by manual 2-axis tilt stages 12 and 13, respectively, and are sequentially supported by an electric X-axis stage 15, an electric Y-axis stage 16 and an electric Z-axis stage 17.

Figure 3:
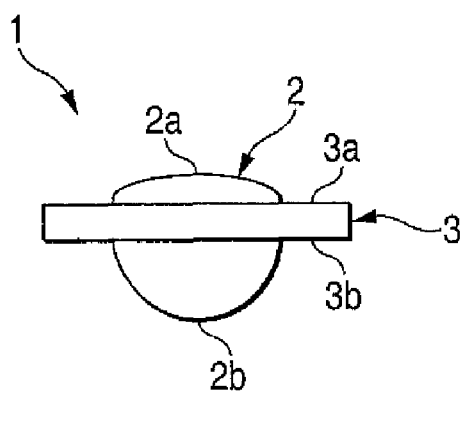
Figure 3:
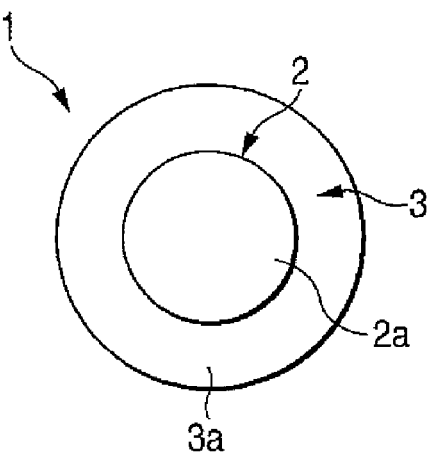

In this embodiment, the lens 1 under test is mounted in an optical sensor as a lens, and includes a lens portion 2 and a projecting portion 3 as shown in FIG. 3. The lens portion 2 has a first lens surface 2a and a second lens surface 2b that are both aspheric. The projecting portion 3 is formed in a flange shape. Its top surface 3a and bottom surface 3b are designed so as to be perpendicular to an optical axis of the lens portion 2.

As shown in FIG. 1, the lens mounting jig 5 is provided with a central window 5a used to measure a transmissive wavefront of the lens portion 2 of the lens 1 under test, projecting-portion windows 5b disposed outside the central window 5a, null-mirror/reflective-flat-surface-portion windows 5c disposed outside the projecting-portion windows 5b. The lens mounting jig 5 supports the projecting portion 3 of the lens 1 under test from the lower side in the drawing.

The null mirror 6 constitutes a reflective null optical element. The null mirror 6 includes a reflective aspherical portion 6a for reflecting back a light flux that once converges and diverges after passing through the lens portion of the lens 1 under test and a reflective flat surface portion 6b provided to be perpendicular to a center axis of the reflective aspherical portion 6a. The rotation angles (inclinations) of the null mirror 6 about the X axis and the Y axis are adjusted by the manual 2-axis tilt stage 12 in the preliminary adjustment step so that the reflective flat surface portion 6b is parallel to the reference surface 4a of the transmissive reference plate 4. Also, the null mirror 6 is adjusted so as to be movable in parallel to the respective directions of the X axis, the Y axis, and the Z axis (extending in the up-down direction in FIG. 1) by the electric X-axis stage 15, the electric Y-axis stage 16, and the electric Z-axis stage 17, respectively. With this configuration, the position of the null mirror 6 is automatically adjusted at the time of measuring the lens 1 under test.

In this embodiment, the manual 2-axis tilt stage 12 constitutes an inclination posture changing unit that changes a relative inclination posture of the lens 1 under test with respect to the null mirror 6. The electric X-, Y-, and Z-axis stages 15, 16, and 17 constitute a 3-axis directional position changing unit for changing 3-axis directional, relative positions of the lens 1 under test with respect to the null mirror 6.

The surface-decenter measuring apparatus of this embodiment is configured to be able to measure the surface decenter of the lens 1 under test that occur due to mold closing errors or the like, separately from the surface tilt of the lens 1 under test. The surface-decenter measuring apparatus includes: a comatic aberration calculating unit that obtains comatic aberration of the lens 1 under test based on an interference fringe image obtained by measuring a transmissive wavefront of the lens 1 under test; a surface-decenter comatic aberration calculating unit that calculates surface-decenter comatic aberration that occurs due to the surface decenter by subtracting surface-tilt comatic aberration that occurs due to surface tilt from the comatic aberration obtained by the comatic aberration calculating unit; and a surface decenter calculating unit that calculates the surface decenter of the lens 1 under test based on the surface-decenter comatic aberration calculated by the surface-decenter comatic aberration calculating unit. Also, the aspheric-lens surface-decenter measuring apparatus further includes a null-optical-element center-axis position determining unit that determines a position of a center axis of the null mirror 6 with respect to the lens 1 under test when the 3-axis directional position changing unit performs adjustment; and a surface-tilt measuring/calculating unit that calculates the surface tilt of the lens 1 under test based on the interference fringe image obtained by measuring a transmissive wavefront of the projecting portion 3. Here, the comatic aberration calculating unit, the surface-decenter comatic aberration calculating unit, the surface decenter calculating unit, the null-optical-element center-axis position determining unit and the surface-tilt measuring/calculating unit are constructed by a CPU within the computer 27 and programs stored in a memory.

Although not shown in the drawings, the surface-decenter measuring apparatus of this embodiment includes a sample stage moving mechanism for automatically performing loading/unloading operations of the lens 1 under test. The sample stage moving mechanism is the same as that described in Japanese Patent Application Nos. 2005-269217 (hereinafter, referred to as "Earlier Application 1"; JP 2007-78593 A, the entire contents of which are incorporated herein by reference in its entirety) and 2006-223668 hereinafter, referred to as "Earlier Application 2"), both of which were filed by Fujinon Corporation, and thus detailed descriptions thereof will be omitted here.

Figure 4:
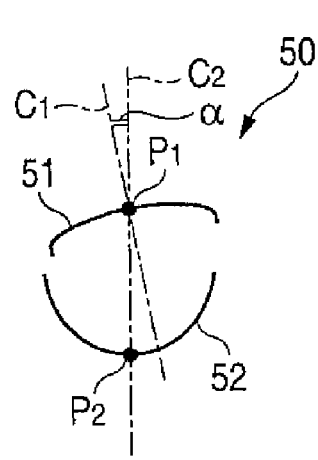
Figure 4:
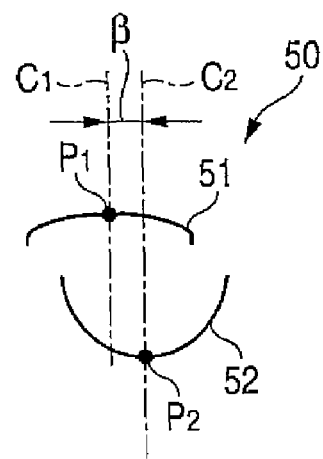
Figure 4:
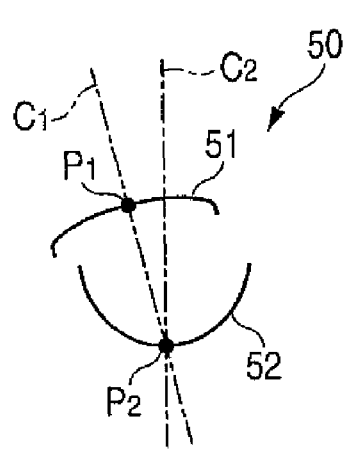

Next, definitions of the surface tilt and the surface decenter in this embodiment will be described. FIGS. 4(A) to 4(C) are diagrams for explaining the surface tilt and the surface decenter, in which FIG. 4(A) shows the state in which only the surface tilt occurs, FIG. 4(B) shows the state in which only the surface decenter occurs, and FIG. 4(C) shows the state in which both the surface tilt and the surface decenter occur. An aspheric lens 50 shown in FIGS. 4(A) to 4(C) is different from the lens 1 under test, but the surface tilt and the surface decenter of the lens 1 under test and a simulation lens under test described later are defined in a similar manner. For simplicity, in FIGS. 4(A) to 4(C), two lens surfaces (a first lens surface 51 and a second lens surface 52) of the aspheric lens 50 are depicted as being separated from each other.

As shown in FIG. 4(A), in this embodiment, a relative inclination angle $\alpha$ between (i) a center axis $C_1$ of the first lens surface 51, which is determined by an aspheric formula of the first lens surface 51, and (ii) a center axis $C_2$ of the second lens surface 52, which is determined by an aspheric formula of the second lens surface 52 (an angle between the two central axes $C_1$ and $C_2$; if the two center axes C1 and C2 don't intersect each other, an angle between respective direction vectors of the two central axes $C_1$ and $C_2$) is defined as the surface tilt of the aspheric lens 50 (a magnitude of the inclination angle $\alpha$ is defined as a surface tilt amount, and an inclination direction of the center axis $C_1$ with respect to the center axis $C_2$ is defined as a surface tilt direction). It is assumed that the first lens surface 51 and the center axis $C_1$ are inclined about a center point $P_1$ (an intersection between the center axis $C_1$ and the first lens surface 51) of the first lens surface 51 as a rotation center. It is also assumed that the second lens surface 52 and the center axis $C_2$ are inclined about a center point $P_2$ (an intersection between the center axis $C_2$ and the second lens surface 52) of the second lens surface 52 as a rotation center.

As shown in FIG. 4(B), in this embodiment, a relative positional misalignment between the center axis $C_1$ of the first lens surface 51 and the center axis $C_2$ of the second lens surface 52 (where the central axes $C_1$ and $C_2$ being parallel to each other) is defined as the surface decenter of the aspheric lens 50. In addition, a distance $\beta$ between the two central axes $C_1$ and $C_2$ is defined as a surface decenter amount, and a positional direction of the center axis $C_1$ with respect to the center axis $C_2$ is defined as a surface decenter direction.

Considering the above assumption that the two central axes $C_1$ and $C_2$ are considered as the rotation centers of the surface tilt, the definition of the surface decenter can be applied as follows: the positional misalignment of the center point $P_1$ of the first lens surface 51 with respect to the center axis $C_2$ of the second lens surface 52 is defined as the surface decenter. In addition, the distance between the center axis $C_2$ and the center point $P_1$ is defined as the surface decenter amount, and the positional direction of the center point $P_1$ with respect to the center axis $C_2$ is defined as the surface decenter direction. That is, as shown in FIG. 4(C), when both the surface tilt and the surface decenter occur in the aspheric lens 50, a relative position misalignment between the two central axes $C_1$ and $C_2$ that remains in a state where the surface tilt is removed from the state shown in FIG. 4(C) (in a state where the first lens surface 51 and the center axis $C_1$ are rotated about the center point $P_1$ as a rotation center so that the two rotation axes $C_1$ and $C_2$ are parallel to each other) is defined as the surface decenter of the aspheric lens 50. This definition has the same meaning as the positional misalignment of the center point $P_1$ with respect to the center axis $C_2$ in the state shown in FIG. 4(C).

Next, the method for measuring surface decenter of an aspheric lens surface (hereinafter, simply referred to as a "surface-decenter measuring method") according to this embodiment of the invention will be described. The surface-decenter measuring method of this embodiment is performed using the above-described surface-decenter measuring apparatus.

<1> First, the relationship between the surface decenter of the lens 1 under test and the comatic aberration (surface-decenter comatic aberration) of the lens 1 under test that occurs due to the surface decenter is obtained by computer simulation (surface-decenter comatic aberration simulation step).

In the surface-decenter comatic aberration simulation step, the computer simulation is performed using (i) a simulation lens under test (hereinafter, referred to as "simulation lens") modeled after the lens 1 under test and (ii) a simulation null optical element (hereinafter, referred to as "simulation null mirror") modeled after the null mirror 6. As a method for setting the relative position of the simulation lens with respect to a center axis of the simulation null mirror, the following two methods (Methods A or B) are conceived. In the following, the procedures of the surface-decenter comatic aberration simulation step will be described for separate cases of Methods A and B.

Method A (a) The simulation lens is set in a point of origin of the XY plane set on the computer (a center axis of a second lens surface (bottom surface) of the simulation lens is controlled so as to be perpendicular to the XY plane in the point of origin of the XY plane).

(b) A predetermined surface decenter amount is input to the simulation lens with a surface decenter direction being set to, for example, the X direction (the first lens surface (top surface) is misaligned (shifted) while the second lens surface is fixed and the center axis of the first lens surface is maintained parallel to the center axis of the second lens surface).

(c) A position of the center axis of the simulation null mirror is input. At this time, the center axis of the simulation null mirror is misaligned with respect to the center axis of the second lens surface by a predetermined amount (the misalignment direction is set to the X direction when the surface decenter direction of the first lens surface of the simulation lens is set to the X direction).

(d) Under the above described setting conditions, simulation for measurement of a transmissive wavefront of the simulation lens is performed so as to calculate a transmissive wavefront aberration $\Phi(x, y)$ of the simulation lens.

(e) Minimum square fitting is performed on the calculated transmissive wavefront aberration $\Phi(x, y)$ using a second-order power series function $F(x, y)$ as specified by the following formula (1) so as to obtain values of the coefficients A, B, and C.

$$F(x,y)=A(x^2+y^2)+Bx+C+D \tag{1}$$

(f) The position of the center axis of the simulation null mirror is input in a misaligned manner so as to be different from that input in the procedure (c). Under such a condition, the values of the coefficients A, B, and C are obtained in a manner similar to the procedures (d) and (e).

(g) From the results obtained through the procedures (e) and (f), a graph (linear function) is obtained that represents a correspondence between (i) a coefficient representing a tilt component in the formula (1) (the coefficient B when misaligned in the x direction) and (iI) the position of the center axis of the simulation null mirror (the coordinate x when misaligned in the x direction).

(h) From the obtained graph, the position of the center axis of the simulation null mirror when the coefficient B becomes equal to 0 is calculated.

(i) The position of the center axis of the simulation null mirror calculated in the procedure (h) is input and simulation for measurement of the transmissive wavefront of the simulation lens to which the surface decenter amount is set in the procedure (b) is performed so as to calculate the transmissive wavefront aberration of the simulation lens, thereby obtaining the comatic aberration (or comatic aberration RMS) of the simulation lens from the transmissive wavefront aberration.

(j) A surface decenter amount different from that input in the procedure (b) is input to the simulation lens. Then, the comatic aberration of the simulation lens when applied with the different surface decenter amount is calculated by performing the procedures (c) to (i).

(k) From the results of the procedure (i) and the procedure (j) (which may be performed plural times), a relationship between the surface dec enter of the simulation lens satisfying the condition that the coefficient B becomes 0 and the surface-decenter comatic aberration occurring due to the surface decenter is obtained.

Method B (a') The simulation lens is set in the point of origin of the XY plane set on the computer (the center axis of the second lens surface (bottom surface) of the simulation lens is set so as to be perpendicular to the XY plane in the point of origin of the XY plane).

(b') A predetermined surface decenter amount is input to the simulation lens (the first lens surface (top surface) is misaligned (shifted) while the second lens surface is fixed and the center axis of the first lens surface is maintained to be parallel to the center axis of the second lens surface).

(c') The position of the center axis of the simulation null mirror is input. At this time, the center axis of the simulation null mirror is misaligned with respect to the center axis of the second lens surface by a predetermined amount.

(d') Under the above described setting conditions, simulation for measurement of a transmissive wavefront of the simulation lens is performed to obtain a transmissive wavefront aberration $\Phi'(x, y)$ of the simulation lens.

(e') The calculated transmissive wavefront aberration $\Phi'(x, y)$ is expanded using a predetermined power series (for example, the Zernike polynomials).

(f') Values of a tilt coefficient and a comatic aberration of the Seidel aberrations (third-order aberration) are obtained from the expanded formula obtained through the procedure (e').

(g') The position of the center axis of the simulation null mirror is input in a misaligned manner so as to be different from that input in the procedure (c'). Under such a condition, a new value of the tilt coefficient is obtained through the procedures (d') to (f').

(h') From the results obtained through the procedures (f') and (g'), a graph (linear function) is obtained that represents a correspondence between the values of the tilt coefficient and the positions of the center axis of the simulation null mirror.

(i') A half value of a difference between the value of the tilt coefficient and the value of the coma coefficient, which are obtained in the procedure (f'), is obtained by the following formula (2):

$$((\text{value of tilt coefficient}) - (\text{value of coma coefficient}))/2 \qquad (2)$$

(j') The position of the center axis of the simulation null mirror is input with being misaligned (shifted) using the value calculated by the formula (2) as a shift coefficient. Under such a condition, the value of the tilt coefficient calculated in the procedure (g') is updated through the procedures (d') to (f').

(k') A half value of a difference between the value of the updated tilt coefficient and the value of the coma coefficient obtained in the procedure (f') is obtained by the above-mentioned formula (2).

(l') By performing the procedures (j') and (k') plural times, the position of the center axis of the simulation null mirror when the value of the tilt coefficient becomes substantially the same as the value of the coma coefficient is obtained from the graph obtained in the procedure (h').

(m') The position of the center axis of the simulation null mirror when the value of the tilt coefficient becomes substantially the same as the value of the coma coefficient is input. Also, simulation for measurement of the transmissive wavefront of the simulation lens to which the surface decenter amount is set in the procedure (b') is performed to obtain the transmissive wavefront aberration of the simulation lens, thereby obtaining the comatic aberration (or comatic aberration RMS) of the simulation lens from the transmissive wavefront aberration.

(n') A surface decenter amount different from that input in the procedure (b') is input to the simulation lens. Then, the comatic aberration of the simulation lens when the different surface decenter amount is given is calculated by performing the procedures (c') to (m').

(o') From the results of the procedure (m') and the procedure (n') (which may be performed plural times), a relationship between the surface decenter of the simulation lens and the surface-decenter comatic aberration that occurs due to the surface decenter under the condition that the value of the tilt coefficient becomes substantially the same as the value of the coma coefficient is calculated.

<2> Subsequent to the above-described surface-decenter comatic aberration simulation step, a relationship between the surface tilt of the lens 1 under test and the comatic aberration (surface-tilt comatic aberration) of the lens 1 under test that occurs due to the surface tilt is calculated by computer simulation (surface-tilt comatic aberration simulation step).

In the surface-tilt comatic aberration simulation step, as a method for setting the relative position of the simulation lens with respect to the center axis of the simulation null mirror, two methods based on Methods A and B are conceived. In the respective procedures, the terms "surface decenter," "surface decenter amount," and "surface decenter direction" described in the procedures of Methods A and B are read as "surface tilt," "surface tilt amount," and "surface tilt direction", respectively. In the case of inputting the surface tilt amount to the simulation lens, the first lens surface is inclined while the second lens surface is fixed and the center axis of the first lens surface is inclined about the center point of the first lens surface as a rotation center.

The results of simulations performed for plural cases using Methods A and B showed that the relationship between the surface decenter and the surface-decenter comatic aberration can be expressed as a linear function as specified by the following formula (3) where u denotes a surface decenter amount and $t_1$ denotes a surface-decenter comatic aberration. Also, the simulation results showed that the relationship between the surface tilt and the surface-tilt comatic aberration can be expressed as a linear function as specified by the following formula (4) where v denotes a surface tilt amount and $t_2$ denotes a surface-tilt comatic aberration. The simulation results further showed that in the case where both the surface decenter and the surface tilt occur, the comatic aberration t can be expressed by the sum ($t = t_1 + t_2$) of the surface-decenter comatic aberration $t_1$ and the surface-tilt comatic aberration $t_2$. In the following formulas (3) and (4), a, b, c, and d are constants.

$$t_1 = au + b \qquad (3)$$

$$t_2 = cv + d \qquad (4)<$$

<3> After the relationship between the surface decenter and the surface-decenter comatic aberration and the relationship between the surface tilt and the surface-tilt comatic aberration are obtained by the above-described computer simulation, a preliminary adjustment is performed on the surface-decenter measuring apparatus before the lens 1 under test is measured. For example, performed are a reference surface inclination adjustment for setting the reference surface 4a of the transmissive reference plate 4 shown in FIG. 1 so as to be perpendicular to the axis of the measurement light flux and an inclination adjustment of the lens mounting jig 5 for setting the lens mounting surface (the top surface in the drawing) of the lens mounting jig 5 so as to be parallel to the reference surface 4a. The detailed procedures of this adjustment are described in Earlier Application 2, and thus detailed descriptions thereof will be omitted.

<4> After the preliminary adjustment is completed, the lens 1 under test is set on the lens mounting jig 5 to measure the surface tilt of the lens 1 under test. The surface tilt is measured in the following procedures.

First, as shown in FIG. 2, the reflective reference plate 7 is moved above the lens 1 under test by the electric X-axis stage 15.

Next, the inclination of the reflective reference plate 7 is adjusted by the manual 2-axis tilt stage 13 so that the reference surface 7a of the reflective reference plate 7 is parallel to the reference surface 4a of the transmissive reference plate 4. The inclination adjustment is performed such that an interference strip formed by interference between a returning light of the light flux applied onto the reference surface 7a of the reflective reference plate 7 after passing through the transmissive reference plate 4 and the returning light from the reference surface 4a of the transmissive reference plate 4 becomes a null fringe. When it is difficult to make the reference surface 7a of the reflective reference plate 7 completely parallel to the reference surface 4a of the transmissive reference plate 4, a relative inclination between the two reference surfaces 4a and 7a may be obtained from the interference fringe in advance and the relative inclination may be corrected later at the time of analyzing the surface tilt of the lens 1 under test.

After the inclination of the reflective reference plate 7 is adjusted, a transmissive wavefront of the projecting portion 3 of the lens 1 under test is measured and analyzed based on the interference strip formed by interference between (i) the returning light of the light flux applied onto the reference surface 7a of the reflective reference plate 7 after passing through the transmissive reference plate 4 and the projecting portion 3 (the returning light passes through the projecting portion 3 after reflected from the reference surface 7a) and (ii) the returning light from the reference surface 4a of the transmissive reference plate 4. From the measurement and analysis, the wedge unevenness in the projecting portion 3 of the lens 1 under test, that is, a relative inclination misalignment between the top surface 3a (front surface) of the projecting portion 3 and the bottom surface 3b (rear surface) thereof is obtained. The relative inclination misalignment is used as the surface tilt of the lens 1 under test (surface tilt measurement step). In this case, the angle between the top surface 3a and the bottom surface 3b is used as the surface tilt amount, and the inclination direction of the top surface 3a with respect to the bottom surface 3b is used as the surface tilt direction.

<5> Based on the obtained surface tilt of the lens 1 under test and the relationship between the surface tilt and the surface-tilt comatic aberration, which is calculated in the procedure <2>, an actual surface-tilt comatic aberration of the lens 1 under test is obtained.

<6> Next, the transmissive wavefront of the lens portion 2 of the lens 1 under test is measured. Then, the comatic aberration of the lens 1 under test is obtained based on an interference fringe image obtained by the measurement (comatic aberration measurement step). This comatic aberration measurement is performed in the following procedures.

First, as shown in FIG. 1, the null mirror 6 instead of the reflective reference plate 7 is moved above the lens 1 under test by the electric X-axis stage 15.

Next, the inclination of the null mirror 6 is adjusted by the manual 2-axis tilt stage 12 so that the center axis of the null mirror 6 is perpendicular to the reference surface 4a of the transmissive reference plate 4. The inclination adjustment is performed so that an interference strip formed by interference between (i) returning light of the light flux applied onto the reflective flat surface portion 6b of the null mirror 6 after passing through the transmissive reference plate 4 and (ii) the returning light from the reference surface 4a of the transmissive reference plate 4 becomes a null fringe.

Then, a relative position of the center axis of the null mirror 6 with respect to the lens 1 under test is determined by the electric X-axis stage 15 and the electric Y-axis stage 16. The relative position is determined such that the wavefront aberration of the lens 1 under test regarding the lens portion 2 is measured while misaligning (shifting) the relative position of the lens 1 under test with respect to the center axis of the null mirror 6 plural times, so as to obtain the relationship between (i) the position of the center axis of the null mirror 6 with respect to the lens 1 under test and (ii) the wavefront aberration of the lens 1 under test, from the measurement results of the wavefront aberrations, thereby determining the relative position based on the obtained relationship. More specifically, the position of the center axis of the null mirror 6 is determined by employing Methods A and B which have been used in the computer simulations performed in the procedures <1> and <2>.

Then, the null mirror 6 is placed in the determined position and the wavefront aberration of the lens 1 under test regarding the lens portion 2 is measured. That is, an interference strip formed by interference between (i) the returning light of the light flux applied onto the reflective aspherical portion 6a of the null mirror 6 after passing through the transmissive reference plate 4 and the lens portion 2 (the returning light passes through the lens portion 2 after being reflected from the reflective aspherical portion 6a) and (ii) the returning light from the reference surface 4a of the transmissive reference plate 4 is analyzed to obtain the actual entire comatic aberration of the lens 1 under test.

<7> The surface-tilt comatic aberration obtained in the procedure <5> is subtracted from the obtained comatic aberration of the lens 1 under test, and the result of subtraction is obtained as the surface-decenter comatic aberration of the lens 1 under test that occurs due to the surface decenter (surface-decenter comatic aberration calculation step).

<8> The surface decenter of the lens 1 under test is calculated based on the obtained surface-decenter comatic aberration and the relationship between the surface decenter and the surface-decenter comatic aberration, calculated in the procedure <1> (surface decenter calculating step).

With the above-described procedures, it is possible to measure the surface decenter of the lens 1 under test with high precision separately from the surface tilt of the lens 1 under test.

In the procedure <4>, it is premised on that when the lens 1 under test is set on the lens mounting jig 5, the bottom surface 3a of the projecting surface 3 of the lens 1 under test is disposed to be parallel to the reference surface 4a of the transmissive reference plate 4, and thereby, the lens 1 under test is appropriately disposed with respect to the optical axis of the interferometer main body 20. However, in practical cases, the lens 1 under test may be disposed to be inclined with respect to the optical axis of the interferometer main body 20 due to some reasons such as a gap between the bottom surface 3a of the projecting surface 3 and the lens mounting jig 5 to cause the lens mounting jig 5 to make a chattering sound. In such cases, the relationship between the inclination of the lens 1 under test with respect to the optical axis of the interferometer main body 20 and the comatic aberration (lens-under-test inclination comatic aberration) that occurs due to the inclination is obtained in advance by computer simulation (lens-under-test inclination simulation step), and the actual inclination of the lens 1 under test is measured from the relative inclination of the bottom surface 3a of the projecting surface 3 with respect to the reference surface 4a (lens-under-test inclination measurement step).

The comatic aberration that occurs due to the actual inclination of the lens 1 under test is calculated from the relationship calculated in the lens-under-test inclination simulation step. The calculated comatic aberration is subtracted from the comatic aberration measured in the comatic aberration measurement step (the procedure <6>).

In the procedure <6>, it is premised on that the inclination adjustment of the null mirror 6 can adjust the center axis of the null mirror 6 so as to be perpendicular to the reference surface 4a of the transmissive reference plate 4. However, there are cases where it is difficult to perform the inclination adjustment with such a high precision that the center axis of the null mirror 6 is perpendicular to the reference surface 4a, and therefore the null mirror 6 is inclined with respect to the optical axis of the interferometer main body 20. In such cases, a relationship between (i) the inclination of the null mirror 6 with respect to the optical axis of the interferometer main body 20 and (ii) the comatic aberration (null-optical-element inclination comatic aberration) that occurs due to the inclination is obtained in advance by computer simulation (null-optical-element inclination simulation step), and the actual inclination of the null mirror 6 with respect to the optical axis of the interferometer main body 20 is measured from the relative inclination of the reflective flat surface portion 6b of the null mirror 6 with respect to the reference surface 4a of the transmissive reference plate 4 (null-optical-element inclination measuring step). The comatic aberration that occurs due to the actual inclination of the null mirror 6 is calculated from the relationship obtained in the null-optical-element inclination simulation step, and the calculated comatic aberration is subtracted from the comatic aberration measured in the comatic aberration measurement step (the procedure <6>).

Although the procedure <6> is described for the case in which the null mirror 6 is provided with the reflective flat surface portion 6b, a null mirror (not shown) that is not provided with the reflective flat surface portion 6b may be used. In such a case, a null optical element inclination determining unit (which is constructed by a CPU within the computer 27 and programs stored in a memory) is provided for determining the inclination of the center axis of the null mirror with respect to the optical axis of the interferometer main body 20. The null optical element inclination determining unit is configured to separate the comatic aberration of the lens 1 under test and the comatic aberration (null-optical-element inclination comatic aberration) that occurs due to the inclination of the center axis of the null mirror with respect to the optical axis of the interferometer main body 20 from the results of measurement of the wavefront aberrations of the lens 1 under test, which are performed by misaligning (changing) the rotation angle of the lens 1 under test with respect to the optical axis of the interferometer main body 20 plural times and to determine the inclination of the center axis of the null mirror so that the null-optical-element inclination comatic aberration is substantially eliminated.

In the above-described embodiment, it has been described for the case of measuring the lens 1 under test provided with the projecting portion 3. However, it is possible to measure a lens under test (not shown) that is not provided with the projecting portion 3. In such a case, a lens inclination determining unit (which is constructed by a CPU within the computer 27 and programs stored in a memory) is provided for determining the inclination of the lens 1 under test with respect to the optical axis of the interferometer main body 20. The lens inclination determining unit is configured to separate the comatic aberration of the lens under test and the comatic aberration (lens-under-test inclination comatic aberration) that occurs due to the inclination of the lens under test with respect to the optical axis of the interferometer main body 20 from the results of measurement of the wavefront aberrations of the lens under test, which are performed by misaligning (changing) the rotation angle of the lens under test with respect to the optical axis of the interferometer main body 20 plural times and to determine the inclination of the lens under test so that the lens-under-test inclination comatic aberration is substantially eliminated.

In the above-described embodiment, the relationship between the surface decenter and the surface-decenter comatic aberration and the relationship between the surface tilt and the surface-tilt comatic aberration have been illustrated as being linear (the case where the relationships are expressed by the above-mentioned formulas (3) and (4)). However, the invention can be applied to the case where the relationships are nonlinear (for example, a case where the coefficient a in the formula (3) is a function of the surface decenter amount u, or a case where the coefficient c in the formula (4) is a function of the surface tilt amount v).

In the above-described embodiment, the aspheric lens both lens surfaces of which are configured as an aspherical surface have been used as a measurement object. However, the invention can be applied to the case in which an aspheric lens of which one lens surface is configured as an aspherical surface and the other lens surface is configured as a spherical surface.

The invention can be applied to the measurement using a transmissive null optical element (null lens) as described in Japanese Patent Application No. 2006-268745, which was filed by Fujinon Corporation.

What is claimed is:

1. A method for measuring surface decenter that is relative positional misalignment between axes of two lens surfaces of a lens under test, at least one of the two lens surfaces of the lens under test being an aspheric surface, the method comprising:

a comatic aberration measurement step of measuring a transmissive wavefront of the lens under test using an interferometer equipped with a null optical element and obtaining a comatic aberration of the lens under test based on an interference fringe image obtained by the measuring;

a surface-decenter comatic aberration calculation step of calculating surface-decenter comatic aberration that occurs due to the surface decenter, by subtracting surface-tilt comatic aberration that is obtained in advance and occurs due to surface tilt from the comatic aberration obtained in the comatic aberration measurement step, wherein the surface tilt is a relative inclination misalignment between the axes of the two lens surfaces; and a surface decenter calculation step of calculating the surface decenter based on the surface-decenter comatic aberration calculated in the surface-decenter comatic aberration calculation step, wherein the comatic aberration measurement step, the surface-decenter comatic aberration calculation step and the surface decenter calculation step are performed in this order.

2. The method according to claim 1, further comprising:

before the surface-decenter comatic aberration calculation step, a surface-tilt comatic aberration simulation step of obtaining a relationship between the surface tilt and the surface-tilt comatic aberration by computer simulation.

3. The according to claim 2, wherein the surface-tilt comatic aberration simulation step comprises a surface-tilt null-optical-element position determination step of determining a position of a center axis of a simulation null optical element with respect to a simulation lens under test in the simulation, and the surface-tilt null-optical-element position determination step comprises performing transmissive wavefront measurement simulations using the simulation null optical element, for the simulation lens under test to which surface tilt is given, with changing a relative position between the center axis of the simulation null optical element and the simulation lens under test plural times during the simulation, obtaining a relationship between the position of the center axis of the simulation null optical element with respect to the simulation lens under test and wavefront aberration of the simulation lens under test, from the respective simulation results, and determining the position of the center axis of the simulation null optical element based on the obtained relationship.

4. The method according to claim 1, further comprising:

before the comatic aberration measurement step, a surface-decenter comatic aberration simulation step of obtaining a relationship between the surface decenter and the surface-decenter comatic aberration by computer simulation.

5. The method according to claim 4, wherein the surface-decenter comatic aberration simulation step comprises a surface-decenter null-optical element position determination step of determining a position of a center axis of a simulation null optical element with respect to a simulation lens under test in the simulation, and the surface-decenter null-optical-element position determination step comprises performing transmissive wavefront measurement simulations using the simulation null optical element, for the simulation lens under test to which surface decenter is given, with changing a relative position between the center axis of the simulation null optical element and the simulation lens under test plural times during the simulation, obtaining a relationship between the position of the center axis of the simulation null optical element with respect to the simulation lens under test and wavefront aberration of the simulation lens under test, from the respective simulation results, and determining the position of the center axis of the simulation null optical element based on the obtained relationship.

6. The method according to claim 1, further comprising, before the surface-decenter comatic aberration calculation step:

a null-optical-element inclination simulation step of obtaining a relationship between an inclination of the null optical element with respect to an optical axis of the interferometer and a null-optical-element inclination comatic aberration that occurs due to the inclination, by computer simulation; and a null-optical-element inclination measurement step of measuring an actual inclination of the null optical element with respect to the optical axis of the interferometer, the method further comprising:

calculating comatic aberration that occurs due to the actual inclination of the null optical element measured in the null-optical-element inclination measurement step, from the relationship obtained in the null-optical-element inclination simulation step; and subtracting the calculated comatic aberration from the comatic aberration measured in the comatic aberration measurement step.

7. The method according to claim 1, further comprising, before the surface-decenter comatic aberration calculation step:

a lens-under-test inclination simulation step of obtaining a relationship between an inclination of the lens under test with respect to an optical axis of the interferometer and a lens-under-test inclination comatic aberration that occurs due to the inclination, by computer simulation; and a lens-under-test inclination measurement step of measuring an actual inclination of the lens under test with respect to the optical axis of the interferometer, the method further comprises:

calculating comatic aberration that occurs due to the actual inclination of the lens under test measured in the lens-under-test inclination measurement step, from the relationship obtained in the lens-under-test inclination simulation step; and subtracting the calculated comatic aberration from the comatic aberration measured in the comatic aberration measurement step.

8. The method according to claim 1, wherein the lens under test has a projecting portion that is provided so as to be perpendicular to the respective axes of the two lens surfaces, the method further comprising, before the surface-decenter comatic aberration calculation step:

a surface tilt measurement step of obtaining the surface tilt by measuring a relative inclination misalignment between a front surface of the projecting portion and a rear surface thereof.

9. An aspheric-lens surface-decenter measuring apparatus for measuring a surface decenter that is relative positional misalignment between axes of two lens surfaces of a lens under test, at least one of the two lens surfaces being an aspheric surface, the apparatus comprising:

an interferometer including a null optical element; and an analyzing device, wherein the analyzing device comprises a comatic aberration calculating unit that obtains a comatic aberration of the lens under test based on an interference fringe image obtained by measuring a transmissive wavefront of the lens under test using the interferometer, a surface-decenter comatic aberration calculating unit that calculates a surface-decenter comatic aberration that occurs due to the surface decenter by subtracting surface-tilt comatic aberration that is obtained in advance and occurs due to surface tilt from the comatic aberration calculated by the comatic aberration calculating unit, wherein the surface tilt is relative inclination misalignment between axes of the two lens surfaces; and a surface decenter calculating unit that calculates the surface decenter based on the surface-decenter comatic aberration calculated by the surface-decenter comatic aberration calculating unit.

10. The apparatus according to claim 9, further comprising:

an inclination posture changing unit that changes a relative inclination posture between the lens under test and the null optical element; and a 3-axis directional position changing unit that changes relative positions between the lens under test and the null optical element in three-axis directions, the three axes being perpendicular to each other.

11. The apparatus according to claim 10, further comprising:
a null-optical-element center-axis position determining unit that determines a position of a center axis of the null optical element with respect to the lens under test when the 3-axis directional position changing unit performs adjustment, wherein
the null-optical-element center-axis position determining unit obtains a relationship between (i) the position of the center axis of the null optical element with respect to the lens under test and (ii) a wavefront aberration of the lens under test, from results of measurement of respective wavefront aberrations of the lens under test, the measurement being performed while changing a relative position of the center axis of the null optical element with respect to the lens under test plural times, and
the null-optical-element center-axis position determining unit determines the position of the center axis of the null optical element based on the obtained relationship.

12. The apparatus according to claim 10, further comprising:
a null optical element inclination determining unit that determines an inclination of the center axis of the null optical element with respect to the optical axis of the interferometer when the inclination posture changing unit performs adjustment, wherein
the null optical element inclination determining unit separates the comatic aberration of the lens under test and null-optical-element inclination comatic aberration that occurs due to the inclination of the center axis of the null optical element with respect to the optical axis of the interferometer, from results of measurement of respective wavefront aberrations of the lens under test, the measurement being performed while changing a rotation angle of the lens under test with respect to the optical axis of the interferometer plural times, and
the null optical element inclination determining unit determines the inclination of the center axis of the null optical element so that the null-optical-element inclination comatic aberration is substantially eliminated.

13. The apparatus according to claim 10, further comprising:
a lens inclination determining unit that determines an inclination of the lens under test with respect to the optical axis of the interferometer when the inclination posture changing unit performs adjustment, wherein
the lens inclination determining unit separates the comatic aberration of the lens under test and a lens-under-test inclination comatic aberration that occurs due to the inclination of the lens under test with respect to the optical axis of the interferometer, from results of measurement of respective wavefront aberrations of the lens under test, the measurement being performed while changing a rotation angle of the lens under test about the optical axis of the interferometer plural times, and
the lens inclination determining unit determines the inclination of the lens under test so that the lens-under-test inclination comatic aberration is substantially eliminated.

14. The apparatus according to claim 9, wherein
the lens under test has a projecting portion that is provided to be perpendicular to the respective axes of the two lens surfaces,
the apparatus further comprising:
a surface-tilt measuring/calculating unit that obtains the surface tilt based on the interference fringe image obtained by measuring a transmissive wavefront of the projecting portion using the interferometer.

15. The apparatus according to claim 9, wherein the null optical element is a reflective null optical element.

16. The apparatus according to claim 9, wherein the null optical element is a transmissive null optical element.

* * * * *